US012636404B2

(12) United States Patent
Shibata et al.

(10) Patent No.: US 12,636,404 B2
(45) Date of Patent: May 26, 2026

(54) METHOD FOR PRODUCING LOCAL HEMOSTASIS MATERIAL, AND LOCAL HEMOSTASIS MATERIAL

(71) Applicants: ARTISAN LAB CO., LTD., Tokyo (JP); NIPRO CORPORATION, Osaka (JP)

(72) Inventors: Kazuhiko Shibata, Tokyo (JP); Noriko Hattori, Osaka (JP); Hiroshi Yoshida, Osaka (JP)

(73) Assignees: ARTISAN LAB CO., LTD., Tokyo (JP); NIPRO CORPORATION, Osaka (JP)

( * ) Notice: Subject to any disclaimer, the term of this patent is extended or adjusted under 35 U.S.C. 154(b) by 850 days.

(21) Appl. No.: 17/789,313

(22) PCT Filed: Dec. 25, 2020

(86) PCT No.: PCT/JP2020/048986

§ 371 (c)(1),
(2) Date: Jun. 27, 2022

(87) PCT Pub. No.: WO2021/132663

PCT Pub. Date: Jul. 1, 2021

(65) Prior Publication Data

US 2023/0158202 A1 May 25, 2023

(30) Foreign Application Priority Data

Dec. 26, 2019 (JP) ................................ 2019-236933

(51) Int. Cl.
*A61L 24/04* (2006.01)

(52) U.S. Cl.
CPC ......... *A61L 24/043* (2013.01); *A61L 2400/04* (2013.01)

(58) Field of Classification Search
CPC ........................................................ C08L 1/02
See application file for complete search history.

(56) References Cited

U.S. PATENT DOCUMENTS

2014/0364712 A1* 12/2014 Lam ........................ A61L 15/18 977/734
2016/0106882 A1 4/2016 Hardy et al.
(Continued)

FOREIGN PATENT DOCUMENTS

EP 3187195 B1 10/2018
JP 2016-522208 A 7/2016
(Continued)

OTHER PUBLICATIONS

English language translation of JP 2017140231 A, Publ. Aug. 17, 2017. (Year: 2017).*
(Continued)

*Primary Examiner* — Dominic Lazaro
(74) *Attorney, Agent, or Firm* — Morgan, Lewis & Bockius LLP

(57) ABSTRACT

Provided is a local hemostasis material, which exerts little influence on the human body, is inexpensive, and exerts a good hemostatic. The local hemostasis material comprises a base material having a first major surface and a layer including cationized cellulose on the first major surface, wherein the layer including cationized cellulose has a thickness of no less than 6.7 μm.

17 Claims, 3 Drawing Sheets

(56) References Cited

U.S. PATENT DOCUMENTS

| | | | |
|---|---|---|---|
| 2017/0258958 | A1 | 9/2017 | Hardy et al. |
| 2017/0258959 | A1 | 9/2017 | Hardy et al. |
| 2021/0085820 | A1 | 3/2021 | Shibata |
| 2021/0205490 | A1 | 7/2021 | Kosonen et al. |

FOREIGN PATENT DOCUMENTS

| | | | | | |
|---|---|---|---|---|---|
| JP | 2017140231 | A | * | 8/2017 | |
| WO | WO-2009130414 | A1 | * | 10/2009 | ........... A61L 31/042 |
| WO | 2019/026177 | A1 | | 2/2019 | |

OTHER PUBLICATIONS

English language translation of WO 2009/130414 A1, Publ. Oct. 29, 2009. (Year: 2009).*
Extended European Search Report dated Nov. 24, 2023, issued in corresponding European Patent Application No. 20906718.0.
International Search Report issued in corresponding International Patent Application No. PCT/JP2020/048986 dated Mar. 2, 2021.

* cited by examiner

METHOD FOR PRODUCING LOCAL HEMOSTASIS MATERIAL, AND LOCAL HEMOSTASIS MATERIAL

TECHNICAL FIELD

This invention relates to a method for producing a local hemostasis material. The invention also relates to a local hemostasis material.

BACKGROUND

Bleeding is the phenomenon of escaping blood from the inside of blood vessels to the outside. Bleeding is caused by a break in blood vessels for some reason. Conventional methods of stopping the bleeding include pressing either the bleeding blood vessels or a part around the blood vessels from outside the body. Compression hemostasis is inconvenient because pressing must keep until bleeding arrests. A hemostatic method of burning the surrounding tissue of bleeding blood vessels, cauterization, may be used during surgery, which causes a problem of damaging the surrounding tissue. Other methods for stopping bleeding include applying compounds such as collagen or oxidized cellulose.

Chitosan is known to exert a high hemostatic effect (Patent Literature 1) and is used as a local hemostatic agent. Chitosan should be used with caution in people with allergies to crustaceans.

Cationized cellulose is a water-soluble polymer that has little influence on the human body and is inexpensive and, accordingly, is widely used in daily necessities such as shampoos. Cationized cellulose was found to possess antibacterial activity and exert a hemostatic effect and is expected to be used as a hemostatic agent (Patent Literature 2).

CITATION LIST

Patent Literature 1: JP 2016-522208 A
Patent Literature 2: JP 2017-140231 A

SUMMARY

In the field of hemostasis, there is a need to provide a local hemostasis material, which exerts little influence on the human body, is inexpensive, and exerts a good hemostatic effect.

Solution to Problem

The present invention was made by finding that a local hemostasis material was produced by applying a cationized cellulose-containing aqueous solution of a predetermined viscosity to at least one surface of a base material and then drying the solution and exerted an excellent hemostatic effect. The present invention specifically provides a local hemostasis material, a method for producing the local hemostasis material, and a mixed liquid for producing the local hemostasis material.

One aspect of the invention provides a method for producing a local hemostasis material, comprising: applying a mixed liquid containing cationized cellulose in solvent to at least one surface of a base material; and removing the solvent, wherein the mixed liquid has a viscosity of no less than 13 mPa·s.

Another aspect of the invention provides a local hemostasis material comprising a base material, wherein a mixed liquid containing cationized cellulose in solvent is applied to at least one surface of the base material, and the mixed liquid has a viscosity of no less than 13 mPa·s.

Another aspect of the invention provides a local hemostasis material, comprising a base material having a first major surface and a layer including cationized cellulose on the first major surface, wherein the layer including cationized cellulose has a thickness of no less than 6.7 μm.

Another aspect of the invention provides a mixed liquid for producing a local hemostasis material, the mixed liquid comprising cationized cellulose in solvent and having a viscosity of no less than 13 mPa·s, wherein the local hemostasis material comprises a base material and a layer including the cationized cellulose on at least one surface of the base material.

BRIEF DESCRIPTION OF DRAWINGS

FIG. 1(*b*) is a front view of the local hemostasis material.

DESCRIPTION OF EMBODIMENTS

Figure 1:
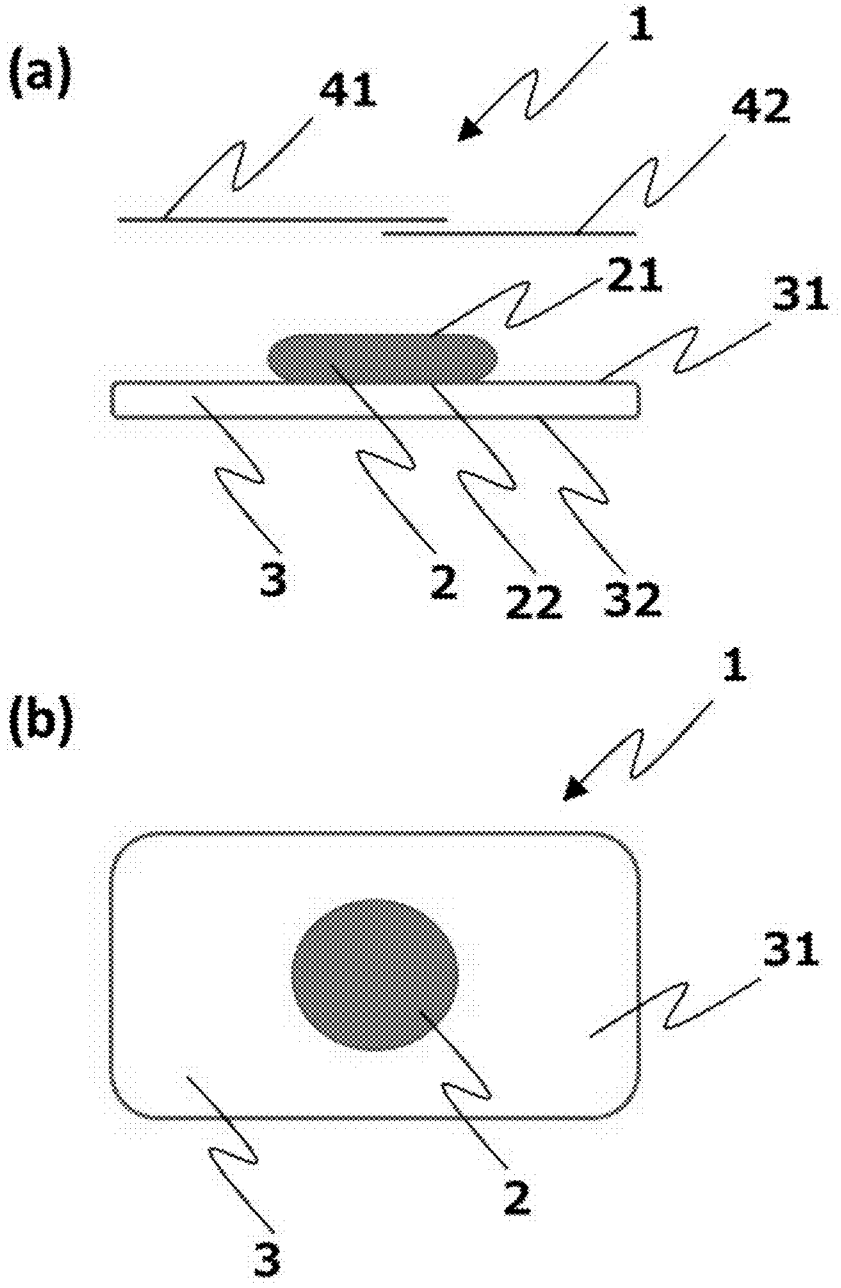
FIG. 1(*a*) is an exploded side view of a local hemostasis material according to an embodiment of the invention.

A "local hemostasis material" in the specification means a material capable of promoting extravascular blood coagulation around a bleeding part, comprising cationized cellulose and base material. The local hemostasis material can be produced by applying a mixed liquid containing cationized cellulose in solvent to at least one surface of the base material and removing the solvent. A local hemostasis material produced by the producing method comprises, but is not limited to, the base material and a layer including cationized cellulose on at least one surface of the base material. In the specification, a local hemostasis material produced by applying the mixed liquid to at least one surface of an absorbent pad and removing the solvent of the mixed liquid is also referred to as a "hemostatic pad."

In an embodiment, the local hemostasis material comprising a layer including cationized cellulose comprises a base material having a first major surface and the layer including cationized cellulose disposed on the first major surface, wherein the layer including cationized cellulose is no less than 6.7 μm in thickness. In an embodiment, the local hemostasis material comprising a layer including cationized cellulose comprises a base material, which has a first major surface and a second major surface opposite the first major surface; the layer including cationized cellulose disposed on the first major surface of the base material, and a support member disposed on the second major surface of the base material, wherein the layer including cationized cellulose is no less than 6.7 μm in thickness.

A "base material" in the specification is any structure capable of holding cationized cellulose on its surface. The base material has, for example, a first major surface and a second major surface opposite the first major surface. The base material has, for example, a shape appropriate for the site to be applied. The base material has, for example, a surface capable of covering a bleeding site. The base material may be, for example, in the form of an absorbent pad or film. The base material may have a surface of various shapes, such as rectangular, square, elliptical, pentagonal, or other polygonal, circular, oval, ellipse, or the like, which can hold cationized cellulose on its surface. The base material can be produced by using, for example, at least one material selected from the group consisting of yarn, weaving yarn, lace, felt, non-woven fabric, natural fiber (e.g., cotton), synthetic fiber (e.g., rayon), synthetic resin (polyethylene terephthalate: PET), and synthetic film. Base materials are commercially available and are, for example, tablet-type cotton ball (Fthree Corporation); gauze; bandage; polyester film such as PET and polybutylene terephthalate; polyolefin film such as polyethylene and polypropylene; polyvinyl chloride film; polycarbonate film; polyurethane film such as polyether urethane and polyester urethane; or laminates of two or more thereof.

An "absorbent pad" in the specification is any structure capable of holding cationized cellulose on its surface and absorbing liquid. The absorbing pad may be, for example, a polygonal prism, a rectangular parallelepiped, or a cylinder having a rectangular or elliptical surface, whose the short side is 1 to 3 cm, the long side is 2 cm to 5 cm, and the thickness is 2 to 10 mm. The absorbing pad may be, for example, a cylinder having a circular surface whose diameter is 1 to 3 cm and the thickness is 2 to 10 mm. The absorbing pad can be produced by, for example, compressing natural fiber such as cotton and silk or synthetic fiber such as polypropylene and/or polyethylene.

A "support member" in the specification has a second surface facing the skin and a first surface opposite the second surface and facing the direction opposite the skin. The support member is not always necessary for practicing the invention. The support member may be various shapes, such as rectangular, square, elliptical, circular, oval, ellipse, heart-shaped, or the like. The support member is, for example, thin, highly flexible or deformable, and water impermeable. The support member may be transparent or opaque. The support member has a thickness of, for example, from 0.05 to 0.2 mm.

The support member may be, for example, polyester film, polyethylene film, stretchable polyurethane elastomer film, or other flexible water-insoluble polymer film known in the art. In other examples, the support member can be produced from polyolefin, vinyl polyethylene acetate, non-woven fabric, rubber, or other materials known in the art.

A first surface of the support member has an adhesive layer capable of adhering to a hemostatic pad and attaching the local hemostasis material to the skin. The adhesive layer includes, but is not limited to, an adhesive biocompatible with the human skin. The adhesive may be water-soluble, water-insoluble, or dispersible in aqueous circumstances and may be, for example, any adhesives available in the field. The adhesive is, for example, an acrylic adhesive. The adhesive layer may have a continuous or discontinuous pattern, such as lines or screens.

A "release sheet" in the specification is a sheet having a first surface facing the first surface of the support member and a second surface opposite the first surface and facing the direction opposite the first surface of the support member. The release sheet covers, for example, the entire first surface of the support member to protect the first surface from contamination during storage or transportation until immediately before the use of the local hemostasis material. A first surface of the release sheet may be coated with silicone resin or the like, the first surface facing the hemostatic pad and the first surface of the support member.

"Cationized cellulose" in the specification means a cellulose-based polymer with cationic groups. Cationized cellulose can be represented, for example, by the following general formula:

[Formula 1]

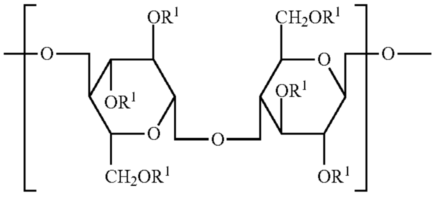

[wherein, at least one $R^1$ is $-R^2-N^+(R^3)(R^4)(R^5)\cdot X^-$, the other $R^1$ of the above $R^1$ is —H, or $-(CH_2CH_2O)_m-H$, $R^2$ is $C_{1-6}$ alkylene, $C_{2-6}$ hydroxyalkylene, $-(CH_2CH_2O)_l-$, or a combination thereof, l is 1 or 2, m is 1 or 2, X− is an anionic group, $R^3$, $R^4$, and $R^5$ are $C_{1-6}$ alkyl, $C_{1-6}$ alkenyl, O—$C_{1-6}$ alkyl, $C_aY_b$ heteroalkyl or heteroalkenyl, wherein a+b is 4 to 6, Y is heteroatom, and when bound to nitrogen atom, Y forms a saturated or unsaturated 5- or 6-membered ring containing the nitrogen atom].

For example, the at least one $R^1$ is $-CH_2CH_2O-CH_2CH(OH)CH_2-N^+(R^3)(R^4)(R^5)\cdot X^-$, wherein $R^3$, $R^4$, and $R^5$ may be methyl group or ethyl group. In another example, the at least one $R^1$ is $-CH_2CH(OH)CH_2N^+(R^3)(R^4)(R^5)\cdot X^-$, wherein $R^3$, $R^4$, and $R^5$ may be methyl group or ethyl group. In another example, the anionic group may be halide ion, phosphate group, carboxyl group, sulfonic acid group, or sulfate group. The halide ion may be fluoride ion, chloride ion, bromide ion, or iodide ion.

Cationized cellulose may be produced according to known methods. In an example, cationized cellulose can be obtained chemically bonding glycidyl trimethylammonium chloride or 3-chloro-2-hydroxypropyl trimethylammonium chloride to hydroxyethyl cellulose partially. In other methods, cationized cellulose can be produced according to the method described in Patent Literature 2. Cationized cellulose is also commercially available and may be, for example, Poise C-60H(Kao Corporation) or Poise C-150H(Kao Corporation).

Cationized cellulose dissolved in the solution is positively charged and interacts with red blood cells and platelets, thereby promoting blood coagulation (Patent Literature 2). For example, at least one of the other $R^1$ may be $-(CH_2CH_2O)_mH$. The cationized cellulose in the example has higher water retention properties and is appropriate for moist wound healing. In another example, any of the hydroxyl groups at positions 2, 4, and 6 of glucose forming the cellulose are modified with a cationized functional group.

A "layer including cationized cellulose" is any structure including cationized cellulose. The layer including cationized cellulose can be formed, for example, by applying a mixed liquid containing cationized cellulose in solvent to a surface of a structure and then removing the solvent from the mixed liquid. The thickness of the cationized cellulose can be measured as a physical distance with a standard measuring instrument such as a micrometer, microscope, caliper, or the like. In specific, the thickness of the cationized cellulose can be measured with a micrometer or microscope. The thickness of the layer including cationized cellulose, may or may not be uniform. When the layer including cationized cellulose has an ununiform thickness, the thickness of the layer including cationized cellulose may be an average of thickness values at five points obtained by measuring the thicknesses at seven different points of one product and excluding the measured data of two points being the maximum value and the minimum value. The seven points for measuring the thickness may be points equally dividing the circumference of the circle, whose radius is a length half the radius of a circle inscribed in the layer including cationized cellulose in the plane view of the main surface of the layer and the center point is equal to the center of the inscribed circle. The plan view is perpendicular to the main surface of the layer including cationized cellulose.

The thickness of the layer including cationized cellulose, may be, for example, no less than 6.7 μm, no less than 7 μm, no less than 8 μm, no less than 9 μm, no less than 10 μm, no less than 15 μm, no less than 16 μm, no less than 17 μm, no less than 18 μm, no less than 19 μm, no less than 20 μm, no less than 25 μm, no less than 30 μm, no less than 50 μm, or no less than 75 μm. The thickness of the layer including cationized cellulose is, for example, no more than 150 μm, no more than 125 μm, no more than 100 μm, no more than 90 μm, or no more than 80 μm. The thickness of the layer including cationized cellulose may be in a range appropriately combining the numerical values described for the layer in the specification, for example, from 6.7 μm to 150 μm, from 7 μm to 150 μm, from 8 μm to 150 μm, from 9 μm to 150 μm, from 10 μm to 150 μm, from 15 μm to 150 μm, from 16 μm to 150 μm, from 17 μm to 150 μm, from 18 μm to 150 μm, from 19 μm to 150 μm, from 20 μm to 150 μm, from 25 μm to 150 μm, from 30 μm to 150 μm, from 50 μm to 150 μm, or from 75 μm to 150 μm.

A "mixed liquid containing cationized cellulose in solvent" in the specification means any liquid comprising cationized cellulose and solvent. The mixed liquid can be prepared, for example, by adding cationized cellulose to solvent. The mixed liquid can be produced, for example, by adding powdered cationized cellulose to water and continuing to stir until the water becomes clear. In another example, the mixed liquid can be produced by diluting cationized cellulose in solvent at a high concentration with solvent.

An embodiment provides a local hemostasis material comprising a base material and a layer including cationized cellulose disposed on at least one surface of the base material. Another embodiment provides a mixed liquid for producing the local hemostasis material, the mixed liquid containing cationized cellulose in solvent and having a viscosity of no less than 13 mPa·s.

The mixed liquid containing cationized cellulose in solvent may include, but not be limited to, other ingredients. The other ingredients may be, for example, antibiotics, analgesics, anti-inflammatory agents, hemostatic agents, skin softeners, hemostatic agents, steroids, softeners, fragrances, coloring agents, cooling agents, warming agents, cellulose or collagen capable of strengthening the layer including cationized cellulose, or a combination thereof. The hemostatic agents may be, for example, collagen, oxidized cellulose, gelatin, thrombin, or a combination thereof. The layer including cationized cellulose and other ingredients can be formed, for example, by applying a mixed liquid containing cationized cellulose and the other ingredients in solvent to a surface of a structure and then removing the solvent from the mixed liquid.

A "solvent" may be, but not be limited to, water or alcohol. The alcohol may be, for example, methanol, ethanol, propanol, or a mixture thereof.

The viscosity of the mixed liquid containing cationized cellulose in solvent is measured with a B-type rotational viscometer. The mixed liquid containing cationized cellulose in solvent preferably has a viscosity of no less than 13 mPa·s. The mixed liquid has a viscosity of no less than 16 mPa·s, no less than 25 mPa·s, no less than 50 mPa·s, or no less than 100 mPa·s. The mixed liquid has, from the viewpoint of a more preferable hemostatic effect, no less than 0.1 Pa·s, no less than 0.2 Pa·s, no less than 0.3 Pa·s, no less than 0.4 Pa·s, no less than 1.8 Pa·s, no less than 2 Pa·s, no less than 2.2 Pa·s, no less than 4 Pa·s, no less than 4.2 Pa·s, no less than 4.5 Pa·s, no less than 8 Pa·s, no less than 9 Pa·s, no less than 10 Pa·s, no less than 11 Pa·s, no less than 50 Pa·s, no less than 60 Pa·s, no less than 70 Pas, no less than 80 Pa·s, no less than 90 Pa·s, no less than 100 Pa·s, or no less than 110 Pa·s.

The viscosity of the mixed liquid containing cationized cellulose is, for example, no more than 150 Pa·s, no more than 140 Pa·s, no more than 130 Pas, no more than 120 Pa·s, or no more than 115 Pa·s. The viscosity of the mixed liquid containing cationized cellulose may be in a range appropriately combining the values of the viscosity described in the specification, for example, from 13 mPa·s to 150 Pa·s, from 16 Pa·s to 150 mPa·s, from 25 mPa·s to 150 Pa·s, from 50 mPa·s to 150 Pas, from 0.1 to 150 Pa·s, from 1 to 150 Pa·s, from 1.8 to 150 Pas, from 2 to 150 Pa·s, from 4 to 150 Pa·s, from 8 to 150 Pa·s, from 10 to 150 Pa·s, from 50 to 150 Pa·s, from 60 to 150 Pa·s, from 70 to 150 Pa·s, from 80 to 150 Pa·s, from 90 to 150 Pa·s, from 100 to 150 Pas, or from 110 to 150 Pa·s.

The molecular weight of cationized cellulose is determined according to the copper ethylenediamine method (JIS 8215). A mixed liquid containing cationized cellulose, whose molecular weight is larger, tends to have a viscosity greater than that of a mixed liquid containing cationized cellulose, whose molecular weight is smaller, at the same concentration (w/w %). A mixed liquid of a predetermined viscosity can be obtained using cationized cellulose having a large molecular weight at a small amount compared to the case where cationized cellulose having a smaller molecular weight is used. The molecular weight of cationized cellulose is, for example, no less than 600,000, no less than 800,000, preferably no less than 1,000,000, no less than 1,200,000, no less than 1,400,000, and more preferably no less than 1,500,000.

Cationized cellulose has a molecular weight of, for example, no more than 3,000,000, no more than 2,500,000, or no more than 2,000,000. The molecular weight of cationized cellulose may be in a range appropriately combining the values of the molecular weight described in the specification, for example, from 600,000 to 3,000,000, from 800,000 to 3,000,000, from 1,000,000 to 3,000,000, from 1,200,000 to 3,000,000, from 1,400,000 to 3,000,000, or from 1,500,000 to 3,000,000.

The mixed liquid containing cationized cellulose can be applied to at least one surface of base material with the use of an instrument, such as a dispensing device, spatula, or the like. The mixed liquid containing cationized cellulose in solvent can be applied to the at least one surface of the base material so that the applied area in total can be, for example, no less than 50%, no less than 60%, no less than 70%, no less than 80%, no less than 90%, no less than 95%, no less than 97%, no less than 99%, or 100%.

The solvent of the mixed liquid applied to the base material is removed, for example, according to known methods for removing solvents such as water or alcohol. The solvent of the mixed liquid applied to the base material may be removed, for example, by placing the base material in a sealed container with a drying agent such as silica gel, by heating, or by placing the base material under reduced pressure, or by a combination thereof.

The solvent of the mixed liquid applied to the base material is not always required to be removed wholly by the removal process described above. In an example, the solvent in the mixed liquid applied to the base material may be removed by no less than 60%, no less than 70%, no less than 80%, no less than 90%, no less than 95%, or 100%. The percentage of solvent removal is obtained, for example, by calculating the weight of the solvent removed from the weights of the base material before and after the removal process and dividing the removed solvent's weight by the weight of the solvent included in the mixed liquid applied to the base material.

In an embodiment, a local hemostasis material comprises, for example, a base material and a layer including cationized cellulose disposed on at least one surface of the base material.

Superior hemostatic effects of the local hemostasis material according to an embodiment of the present invention were demonstrated and are described in the following Examples. It is considered that cationized cellulose included in the layer is positively charged. The positive charge facilitates the interaction of negatively charged red blood cells and platelets in the blood with the layer including cationized cellulose, thereby leading to the superior hemostatic effects of the local hemostasis material.

In an example, a hemostatic pad comprises a base material and a layer including cationized cellulose disposed on at least one surface of the base material. The layer including cationized cellulose can be prepared by, for example, applying a mixed liquid containing cationized cellulose in the solvent described in the specification to at least one surface of the base material and removing the solvent. An embodiment of the invention provides a mixed liquid for producing a local hemostasis material, the mixed liquid comprising cationized cellulose in the solvent and having a viscosity of no less than 13 mPa·s, wherein the local hemostasis material comprises a base material and a layer including the cationized cellulose disposed on at least one surface of the base material.

With reference to FIG. 1, a local hemostasis material 1 according to an embodiment of the invention is explained. However, the embodiment is a mere example of the invention and does not limit the scope of the invention recited in the accompanying claims in any manner.

FIG. 1(*a*) shows a local hemostasis material 1 comprising a hemostatic pad 2. The hemostatic pad 2 comprises an absorbent pad and cationized cellulose. The hemostatic pad 2 is an absorbent pad comprising a layer including cationized cellulose (not shown). The absorbent pad is a cylindrical cotton tablet. The hemostatic pad 2 has a first surface 21 facing the skin and a second surface 22 facing the direction opposite the skin. The hemostatic pad 2 comprises a layer including cationized cellulose on the first surface 21.

The local hemostasis material 1 comprises a support member 3. The support member 3 has a first surface 31 facing the skin, and a second surface 32 facing the direction opposite the skin. The first surface 31 of the support member 3 is adhered to the second surface 22 of the hemostatic pad 2. The first surface 31 of the support member 3 comprises an adhesive layer, including a biocompatible acrylic adhesive.

The local hemostasis material comprises a first release sheet 41 and a second release sheet 42. The first release sheet 41 covers the left half of the first surface 21 of the hemostatic pad 2 and the left half of the first surface 31 of the support member 3, as shown in FIG. 1(*a*). The second release sheet 42 covers the right half of the first surface 31 of the hemostatic pad 2, and the right half of the first surface 31 of the support member 3. In the embodiment, the release sheet is composed of two sheets in combination, but the number of sheets is not limited to two. The release sheet may be one sheet covering the entire first surface of the hemostatic pad 2 and the first surface 31 of the support member 3 or may be three sheets or more sheets covering them.

FIG. 1(*b*) shows the local hemostasis material 1, which comprises the hemostatic pad 2 disposed on the center of the support member 3.

Specific examples are described below. However, these examples are merely preferred embodiments of the invention and do not limit the scope of the invention recited in the accompanying claims.

EXAMPLE

Example 1

(Preparation of Aqueous Solutions Containing Cationized Cellulose)

Poise C-60H described below was added to purified water and stirred to prepare 1 w/w %, 2 w/w %, 4 w/w %, 0.2 w/w %, 0.3 w/%, 0.4 w/w %, and 0.5 w/w % cationized cellulose aqueous solutions (referred to as Test solutions 1, 2, 3, 7, 8, 9, and 10, respectively). In the same manner as the above, 1 w/w %, 2 w/w %, and 4 w/w % cationized cellulose aqueous solutions were prepared using Poise C-150L (referred to as Test solutions 4, 5, and 6, respectively).

TABLE 1

| Product | Company | Active ingredient * | Molecular weight | Form |
|---|---|---|---|---|
| Poise C-60H | Kao Corporation | 90%. | 600,000 | powder |
| Poise C-150L | Kao Corporation | 90%. | 1,500,000 | powder |

* O-[2-hydroxy-3-(trimethylammonio)propyl]hydroxyethylcellulose]chloride (Viscosity Measurement)

The viscosities of the prepared Test solutions 1-10 were measured with a B-type rotational viscometer. The measured values are summarized below.

TABLE 2

| Test solution | Concentration [w/w %] | Molecular weight | Viscosity* [mPa-s]. Estimated value | Measured value |
|---|---|---|---|---|
| 1 | 1 | 600,000 | 60 | 41.9 |
| 2 | 2 | 600,000 | 600 | 267 |
| 3 | 4 | 600,000 | 15,000 | 4,192 |
| 4 | 1 | 1,500,000 | 2,000 | 1256 |
| 5 | 2 | 1,500,000 | 15,000 | 10,100 |
| 6 | 4 | 1,500,000 | 100,000 | >100,000 |
| 7 | 0.2 | 600,000 | 6 | 8.2 |
| 8 | 0.3 | 600,000 | — | 10.6 |
| 9 | 0.4 | 600,000 | — | 13 |
| 10 | 0.5 | 600,000 | 20 | 15.8 |

As shown in Table 2, Test solution 1 had a viscosity of 41.9 mPa·s (measured value), and Test solution 2 had a viscosity of 267 mPa·s (measured value). The molecular weight of the cationized cellulose in Test solution 1 was 600,000, which is equal to that in Test solution 2. The concentration of the cationized cellulose in Test solution 1 was 1 w/w %, whereas Test solution 2 was 2 w/w %. The results indicate that solutions containing cationized cellulose at higher concentrations have higher viscosities. Indeed, Test solution 3, which contained an even higher concentration of cationized cellulose (4 w/w %), had a higher viscosity (4, 192 mPa·s), even though the solution contained the cationized cellulose of the same molecular weight 600,000 (Table 2).

Test solution 2 had a viscosity of 267 mPa·s (measured value), while Test solution 5 had a viscosity of 10, 100 mPa·s (measured value). The concentration of the cationized cellulose in Test solution 2 was 2 [w/w %], the same as in Test solution 5, while the molecular weight of the cationized cellulose in Test solution 2 was 600,000, whereas Test solution 5 was 1,500,000. The results indicate that aqueous solutions containing cationized cellulose having higher molecular weights have higher viscosities.

(Preparation of Local Hemostasis Material)

Test solution 1 of 0.05 g was applied with a dispensing device to one surface of compressed cotton, a disk-shaped (diameter 10 mm×height 1.5 mm) band-aid (NIPRO Empad S size). The compressed cotton was placed in a sealed container with silica gel and dried overnight at room temperature to produce a hemostatic pad 1. Hemostatic pads 2-6 were prepared with Test solutions 2-6, respectively, in the same manner as the above in which Test solution 1 was used.

(Hemostasis Test)

Whole blood samples A-E were collected from five volunteers. A few drops of each whole blood sample A-E were dropped on glass plates, and local hemostasis materials shown below were placed on the blood drops, allowing them to contact with the glass plate via the blood.

TABLE 3

| Local hemostatic material | Company | Active ingredient | Base material |
|---|---|---|---|
| Hemostatic pad | — | cationized cellulose | tablet cotton |
| Empad S | NIPRO Corporation | (None) | non-woven fabric |
| Neoplaster CMC | NIPRO Corporation | carboxymethyl cellulose | non-woven fabric |
| HemConDot | ZERIA Pharmaceutical Co., Ltd. | Chitosan, acetic acid | cotton pad |
| Hemostatic Bond Plus | TOY MEDICAL Co., Ltd. | alginate | Alginate-containing non-woven fabric |

Figure 2:
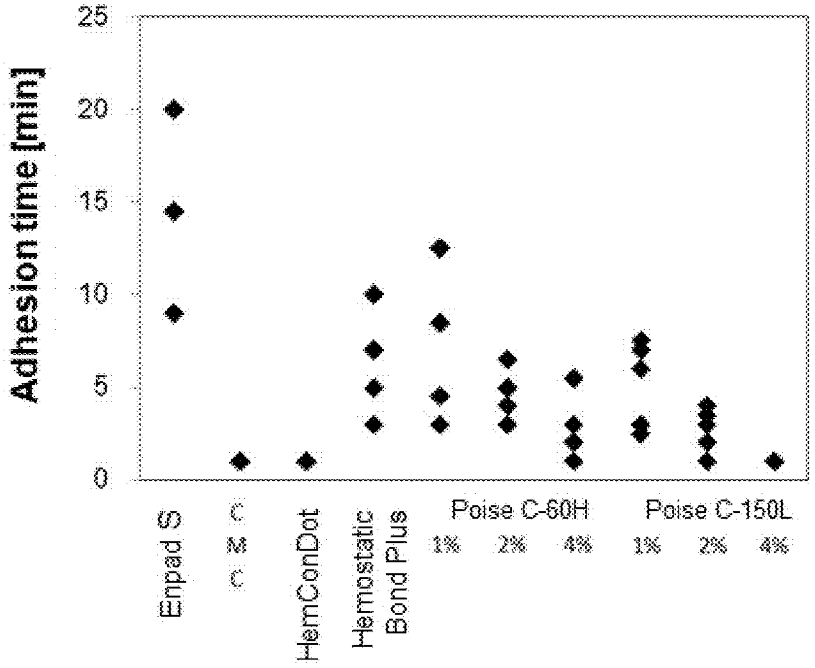
FIG. 2 is a scatter graph showing the adhesion times of several hemostatic pads to a glass plate via blood.

The local hemostasis materials were pressed against the glass plate for 30 seconds after the local hemostasis materials were placed on the glass plate. After that, the time until the local hemostasis material did not move (adhesion time) was recorded at 30-second intervals. In the hemostasis test, a shorter time (min) for the local hemostasis material to adhere to the glass plate means a higher hemostatic effect. The results for each local hemostasis material are summarized below (Table 4 and FIG. 2). A two-tailed t-test was performed for Empad S, with correspondence for each test result.

TABLE 4

| Local hemostatic material | Blood sample A | B | C | D | E | Average | t-test |
|---|---|---|---|---|---|---|---|
| Empad S | 14.5 | 9.0 | 20.0 | 20.0 | 14.5 | 15.6 | |
| Neoplaster CMC | 1.0 | 1.0 | 1.0 | 1.0 | 1.0 | 1.0 | 0.002 ** |
| HemConDot | 1.0 | 1.0 | 1.0 | 1.0 | 1.0 | 1.0 | 0.002 ** |
| Hemostatic Bond Plus | 10.0 | 3.0 | 7.0 | 5.0 | — | 6.3 | 0.033 * |
| Hemostatic pad 1 | 8.5 | 8.5 | 3.0 | 4.5 | 12.5 | 7.4 | 0.074 n.s |
| Hemostatic pad 2 | 5.0 | 6.5 | 3.0 | 4.0 | 5.0 | 4.7 | 0.014 * |
| Hemostatic pad 3 | 1.0 | 2.0 | 5.5 | 5.5 | 3.0 | 3.4 | 0.001 ** |
| Hemostatic pad 4 | 3.0 | 7.5 | 7.0 | 2.5 | 6.0 | 5.2 | 0.017 * |
| Hemostatic pad 5 | 1.0 | 4.0 | 3.0 | 3.5 | 2.0 | 2.7 | 0.004 ** |
| Hemostatic pad 6 | 1.0 | 1.0 | 1.0 | 1.0 | 1.0 | 1.0 | 0.002 ** |

* $p < 0.05$

** $p < 0.01$ n. s. not significant

As shown in Table 4, the protective covering Empad S took 15.6 minutes on average to adhere to the glass plate in the Hemostasis test. In contrast, the hemostatic pads 1-6 all adhered to the glass plate in shorter times (7.4 min to 1.0 min on average). The results indicate that the cationized cellulose-containing hemostatic pads exert a superior hemostatic effect.

Hemostatic Bond Plus, whose alginate may provide stop bleeding, took an average adhesion time of 6.3 minutes, while the hemostatic pads 1-6 took similar or shorter adhesion times (7.4 min to 1.0 min on average). The results indicate that the cationized cellulose-containing hemostatic pads that may provide a hemostatic effect exert similar or better effects than the alginate-containing local hemostasis materials.

Hemostatic pads 2-6 took significantly shorter adhesion times than the adhesion times with Empad S (Table 4, t-test). The results indicate that cationized cellulose-containing local hemostasis materials that may provide a hemostatic effect exert a superior hemostatic effect.

Hemostatic pads 2-6 took shorter adhesion times (5.2 min to 1.0 min on average) than the adhesion time with the use of hemostatic pad 1 (7.4 min on average). In comparison to the viscosity of hemostatic pad 1 (60 mPa·s; estimated value) shown in Table 2, the hemostatic pads 2-6 all had higher viscosities (267 mPa·s to >100 mPa·s) (Table 5). The results indicate that in cationized cellulose-containing local hemostasis materials that may provide hemostatic effects, the viscosities of aqueous solutions used to prepare local hemostasis materials correlate with that of the local hemostasis materials prepared by drying the solutions.

(Relationship Between Viscosity and Adhesion Time)

The viscosity of each hemostatic pad in Table 2 and the average adhesion time of each hemostatic pad in Table 4 are summarized below (Table 5 and FIG. 3).

TABLE 5

| Local hemostatic agent | Viscosity* [mPa · s], Measured value | Average | t-test |
|---|---|---|---|
| Empad S | | 15.6 | |
| Hemostatic pad 1 | 42 | 7.4 | 0.074 n.s |
| Hemostatic pad 2 | 267 | 4.7 | 0.014 * |
| Hemostatic pad 3 | 4,192 | 3.4 | 0.001 ** |
| Hemostatic pad 4 | 1256 | 5.2 | 0.017 * |

TABLE 5-continued

| Local hemostatic agent | Viscosity* [mPa · s], Measured value | Average | t-test |
|---|---|---|---|
| Hemostatic pad 5 | 10,100 | 2.7 | 0.004 ** |
| Hemostatic pad 6 | > 100,000 | 1.0 | 0.002 ** |

Figure 3:
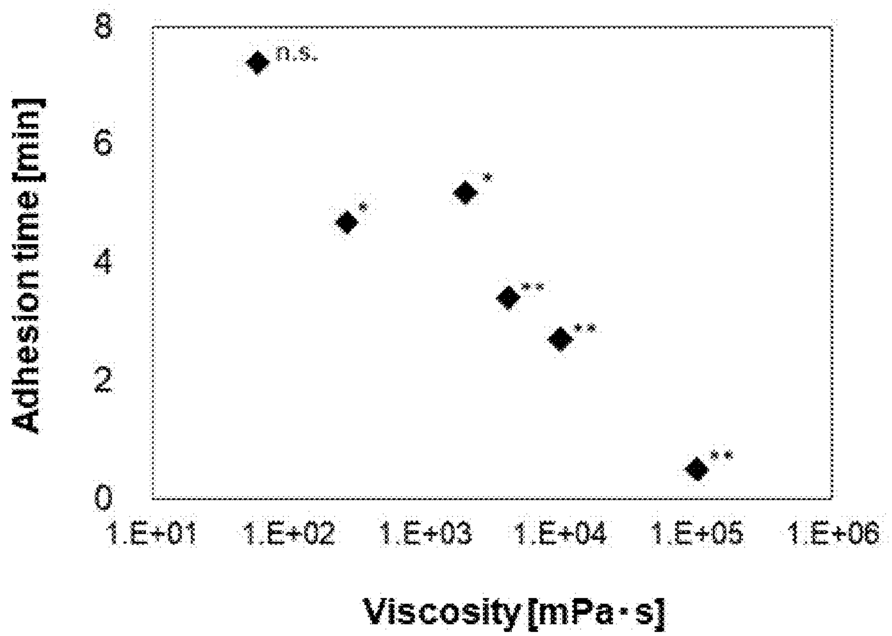
FIG. 3 is a scatter graph showing a relationship between the viscosities of cationized cellulose aqueous solutions and the times for hemostatic pads produced using the solutions to adhere to a glass plate via blood.

FIG. 3 shows shorter adhesion times as the viscosities of the local hemostasis materials increased. The results indicate that the viscosities of the aqueous solutions used to produce the local hemostasis materials affect the hemostatic effects of the local hemostasis materials and that the higher the viscosities of the solutions, the better the local hemostasis materials exert hemostatic effects. For example, the hemostatic pad 6 produced by Test solution 6 of a higher viscosity exerted a superior hemostatic effect (Table 4), similar to the local hemostasis materials (Neoplaster CMC or HemCon-Dot) expected to exert superior hemostatic effects due to carboxymethylcellulose or chitosan.

Example 2

(Thickness of the Layer Including Cationized Cellulose)

Test solution 10 of 0.0637 mg was applied with a dispensing device to one surface of a square PET film of 10 mm. The PET film was placed in a sealed container with silica gel and dried overnight at room temperature to produce hemostatic film 1. Test films 2, 3, 5, and 6 were prepared using Test solutions 1, 4, 2, and 6 in the same manner as the above. An aqueous solution containing cationized cellulose (1.5 w/w %) was prepared by the cationized cellulose (Poise C-60H), whose molecular weight is 600,000, used in EXAMPLE 1. Hemostatic film 4 was prepared using the prepared cationized cellulose-containing aqueous solution of 1.5 w/w %, in the same manner as the above. Six sheets of each hemostatic film were prepared.

The thicknesses of the layer including cationized cellulose disposed on one surface of hemostatic films 1-6, were measured with a micrometer (MITUTOYO Corporation). Specifically, the thicknesses were measured at seven points on each film, and two points being maximum and minimum values were excluded from the seven points to calculate the average thickness of each hemostatic film from the 5 points' thicknesses. By subtracting the thickness [μm] of the PET film to which Test solution was not applied (control) from the thickness [μm] of each hemostatic film 1-6, the thickness [μm] of the layer including cationized cellulose was calculated. The results are summarized below (Table 6).

TABLE 6

| | The thickness of the layer including cationized cellulose [μm] | | | | | |
|---|---|---|---|---|---|---|
| | Hemostatic film 1 | Hemostatic film 2 | Hemostatic film 3 | Hemostatic film 4 | Hemostatic film 5 | Hemostatic film 6 |
| 1 | 8.6 | 14.6 | 16.0 | 19.4 | 25.2 | 69.8 |
| 2 | 12.0 | 16.4 | 18.6 | 17.6 | 27.6 | 78.0 |
| 3 | 9.2 | 15.6 | 8.2 | 18.6 | 25.8 | 69.8 |
| 4 | 10.8 | 15.2 | 16.0 | 21.4 | 22.6 | 57.8 |
| 5 | 10.8 | 15.4 | 17.6 | 16.4 | 22.2 | 91.0 |
| 6 | 12.2 | 18.6 | 19.4 | 23.6 | 20.4 | 82.0 |
| average | 10.6 | 16.0 | 16.0 | 19.5 | 24.0 | 74.7 |

Whole blood samples F and G were collected from two volunteers. The whole blood samples F and G were used (n=3) to measure the time (min) for the hemostatic film to adhere to the glass plate in the same manner as in Example 1. The results are shown below (Table 7). T-test was conducted for PET films.

TABLE 7

| Hemostatic film | blood sample F-1 | F-2 | F-3 | G-1 | G-2 | G-3 | Average | p-value | t-test | The thickness of the layer including cationized cellulose [μm] | Viscosity [mPa · s] |
|---|---|---|---|---|---|---|---|---|---|---|---|
| PET film | 5.0 | 6.0 | 4.5 | 4.0 | 5.0 | 5.5 | 5.0 | — | — | 0 | |
| Hemostatic film 1 | 3.5 | 4.0 | 4.0 | 4.0 | 4.5 | 4.0 | 4.0 | 0.010 | * | 10.6 | 15.8 |
| Hemostatic film 2 | 3.5 | 3.0 | 0.5 | 3.0 | 2.0 | 1.5 | 2.3 | <0.01 | ** | 16.0 | 42 |
| Hemostatic film 3 | 1.0 | 1.0 | 1.0 | 2.0 | 1.0 | 1.0 | 1.2 | <0.01 | ** | 16.0 | 1,256 |
| Hemostatic film 4 | 2.0 | 1.5 | 0.5 | 1.0 | 1.0 | 2.5 | 1.4 | <0.01 | ** | 19.5 | |
| Hemostatic film 5 | 0.5 | 0.5 | 1.5 | 1.5 | 1.0 | 1.5 | 1.1 | <0.01 | ** | 24.0 | 267 |
| Hemostatic film 6 | 0.5 | 0.5 | 0.5 | 0.5 | 0.5 | 0.5 | 0.5 | <0.01 | ** | 74.7 | 100,000 |

* $p < 0.05$
** $p < 0.01$
n.s. not significant

Figure 4:
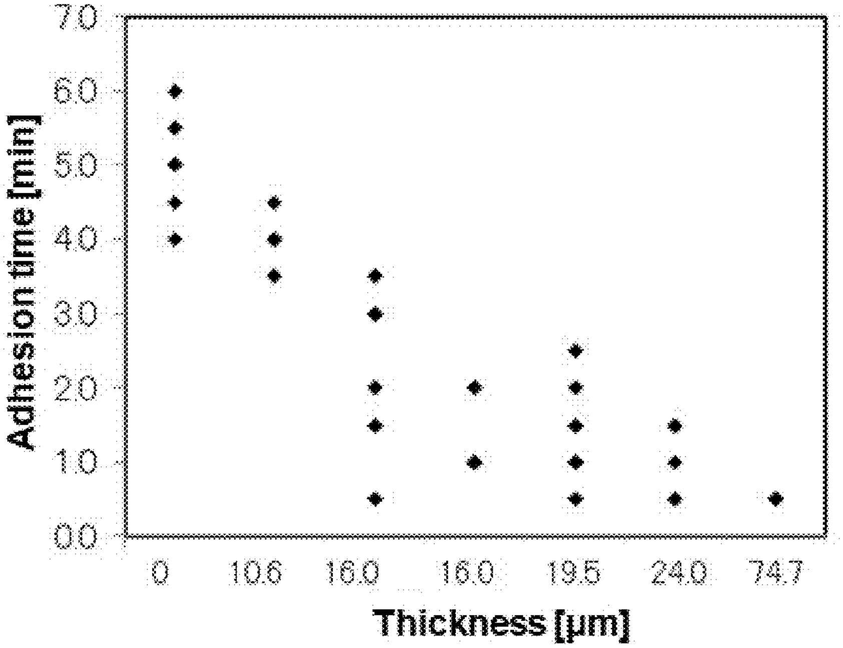
FIG. 4 is a graph showing a relationship between the thicknesses of layers including cationized cellulose, and the times for hemostatic films to adhere to a glass plate via blood.

The thicknesses and adhesion times of the layers including cationized cellulose demonstrated in EXAMPLE 2, are summarized in FIG. 4, which shows shorter adhesion times as the thicknesses of the local hemostasis materials increased. The results indicate that the thickness of the layer including cationized cellulose of the local hemostasis material affects its hemostatic effect; specifically, the greater the thicknesses, the better the local hemostasis materials exert hemostatic effects.

Example 3

(Thickness of the Layer Including Cationized Cellulose)

Hemostatic films 7-9 were prepared using Test solutions 7-9 in the same manner as in Example 2. The thicknesses [μm] of hemostatic films 7-9 were measured in the same manner as in Example 2. The results are summarized below (Table 8).

TABLE 8

| | The thickness of the layer including cationized cellulose [μm] Hemostatic film 7 | Hemostatic film 8 | Hemostatic film 9 |
|---|---|---|---|
| 1 | 1.2 | 7.2 | 8.6 |
| 2 | 0.8 | 6.6 | 3.4 |
| 3 | 6.0 | 4.8 | 6.2 |
| 4 | 0.2 | 6.4 | 2.2 |
| 5 | 1.4 | 8.6 | 8.4 |
| 6 | 3.6 | 4.6 | 11.2 |
| average | 2.2 | 6.4 | 6.7 |

The time (min) for hemostatic films 7-9 to adhere to the glass plate was measured in the same manner as in Example 2. The results are summarized below (Table 9). T-test was conducted for PET films.

TABLE 9

| hemostatic film | blood sample F-1 | F-2 | F-3 | G-1 | G-2 | G-3 | Average | p-value | t-test | The thickness of layer containing cationized cellulose (μm) | Viscosity (mPa · s) |
|---|---|---|---|---|---|---|---|---|---|---|---|
| PET film | 4.5 | 4.5 | 5.5 | 4.5 | 4.5 | 5.0 | 4.8 | — | — | 0.0 | |
| Hemostatic film 7 | 4.5 | 4.0 | 4.5 | 5.0 | 4.0 | 2.5 | 4.1 | 0.119 | n.s. | 2.2 | 8.2 |
| Hemostatic film 8 | 5.0 | 3.5 | 3.5 | 4.5 | 3.0 | 4.5 | 4.0 | 0.063 | n.s. | 6.4 | 10.6 |
| Hemostatic film 9 | 4.0 | 3.0 | 4.5 | 3.5 | 4.0 | 4.5 | 3.9 | 0.018 | * | 6.7 | 13.0 |

* $p < 0.05$
** $p < 0.01$
n.s. not significant

Table 9 shows that the local hemostasis material whose cationized cellulose-containing layer has a thickness of 6.7 μm exerted a hemostatic effect.

The invention claimed is:

1. A local hemostasis material, comprising a base material having a first major surface and a layer including cationized cellulose on the first major surface, wherein the layer including cationized cellulose has a thickness of 50 μm to 150 μm;

the cationized cellulose has a molecular weight of 1,000,000 to 3,000,000; and the cationized cellulose is water soluble and is represented by Formula (I):

(Formula I)

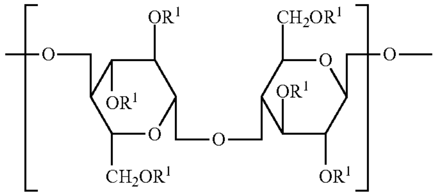

in which at least one $R^1$ is $R^2—N^+(R^3)(R^4)(R^5)·X^-$, the other $R^1$ of the above $R^1$ is H, or $(CH_2CH_2O)_m—H$, $R^2$ is $C_{1-6}$ alkylene, $C_{2-6}$ hydroxyalkylene, $(CH_2CH_2O)_l$, or a combination thereof, l is 1 or 2, m is 1 or 2, X is an anionic group, $R^3$, $R^4$, and $R^5$ are independently $C_{1-6}$ alkyl, $C_{1-6}$ alkenyl, $O—C_{1-6}$ alkyl, $C_aY_b$ heteroalkyl, or heteroalkenyl, a+b is 4 to 6, Y is heteroatom, and when bound to nitrogen atom, Y forms a saturated or unsaturated 5- or 6-membered ring containing the nitrogen atom.

2. The local hemostasis material according to claim 1, wherein the base material is a structure of cotton, polyethylene terephthalate (PET), rayon, or a composite thereof.

3. The local hemostasis material according to claim 1, wherein l is 1.

4. The local hemostasis material according to claim 1, wherein l is 2.

5. The local hemostasis material according to claim 1, wherein m is 1.

6. The local hemostasis material according to claim 1, wherein Y, when bound to nitrogen atom, forms a saturated 5-membered ring containing the nitrogen atom.

7. The local hemostasis material according to claim 1, wherein Y, when bound to nitrogen atom, forms a saturated 6-membered ring containing the nitrogen atom.

8. The local hemostasis material according to claim 1, wherein Y, when bound to nitrogen atom, forms an unsaturated 5- or 6-membered ring containing the nitrogen atom.

9. A method for producing a local hemostasis material, comprising: applying a mixed liquid containing cationized cellulose in solvent to at least one surface of a base material; and removing the solvent to form a layer including the cationized cellulose, wherein the mixed liquid has a viscosity of no less than 13 mPa·s at room temperature, the layer including the cationized cellulose has a thickness of 50 μm to 150 μm;

the cationized cellulose has a molecular weight of 1,000,000 to 3,000,000; and the cationized cellulose is water soluble and is represented by Formula (I):

(Formula I)

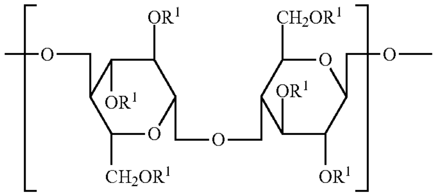

in which at least one $R^1$ is $R^2—N^+(R^3)(R^4)(R^5)·X^-$, the other $R^1$ of the above $R^1$ is H, or $(CH_2CH_2O)_m—H$, $R^2$ is $C_{1-6}$ alkylene, $C_{2-6}$ hydroxyalkylene, $(CH_2CH_2O)_l$, or a combination thereof, l is 1 or 2, m is 1 or 2, X− is an anionic group, $R^3$, $R^4$, and $R^5$ are independently $C_{1-6}$ alkyl, $C_{1-6}$ alkenyl, O—$C_{1-6}$ alkyl, $C_aY_b$ heteroalkyl, or heteroalkenyl, a+b is 4 to 6, Y is heteroatom, and when bound to nitrogen atom, Y forms a saturated or unsaturated 5- or 6-membered ring containing the nitrogen atom.

10. The method according to claim 9, wherein the solvent is water, alcohol, or a mixture thereof.

11. The method according to claim 10, wherein the base material is a structure of cotton, PET, rayon, or a composite thereof.

12. The method according to claim 9, wherein the base material is a structure of cotton, PET, rayon, or a composite thereof.

13. The method according to claim 9, wherein the viscosity of the mixed liquid ranges from 10 Pa·s to 150 Pa·s at room temperature.

14. The method according to claim 9, wherein m is 2.

15. The method according to claim 9, wherein l is 1.

16. The method according to claim 9, wherein l is 2.

17. The method according to claim 9, wherein m is 1.

* * * * *